United States Patent
Bainton

(10) Patent No.: US 7,361,161 B2
(45) Date of Patent: Apr. 22, 2008

(54) MEDICAMENT DELIVERY DEVICE

(75) Inventor: Michael Cameron Bainton, Warwickshire (GB)

(73) Assignee: DCA Design International Limited, Warwick (GB)

(*) Notice: Subject to any disclaimer, the term of this patent is extended or adjusted under 35 U.S.C. 154(b) by 544 days.

(21) Appl. No.: 10/375,097

(22) Filed: Feb. 28, 2003

(65) Prior Publication Data
US 2003/0176841 A1    Sep. 18, 2003

(30) Foreign Application Priority Data
Mar. 8, 2002   (GB) ................. 0205485

(51) Int. Cl.
*A61M 5/00* (2006.01)
(52) U.S. Cl. .................................. 604/207
(58) Field of Classification Search ........... 604/68–71, 604/181, 186, 187, 200, 207, 208, 211, 218, 604/223, 228, 246, 232, 234, 235
See application file for complete search history.

(56) References Cited

U.S. PATENT DOCUMENTS

| | | | |
|---|---|---|---|
| 5,279,586 A * | 1/1994 | Balkwill ............... | 604/207 |
| 5,304,152 A | 4/1994 | Sams | |
| 5,320,609 A | 6/1994 | Haber et al. | |
| 5,423,752 A | 6/1995 | Haber et al. | |
| 5,626,566 A | 5/1997 | Petersen et al. | |
| 6,096,010 A * | 8/2000 | Walters et al. ........... | 604/207 |
| 6,193,698 B1 | 2/2001 | Kirchhofer et al. | |
| 6,221,053 B1 * | 4/2001 | Walters et al. ........... | 604/211 |

FOREIGN PATENT DOCUMENTS

| | | |
|---|---|---|
| EP | 0-368-191 A1 | 5/1990 |
| EP | 368191 * | 5/1990 |
| EP | DE 3645245 * | 1/1994 |
| WO | WO 94/03222 | 2/1994 |

* cited by examiner

*Primary Examiner*—Matthew DeSanto
(74) *Attorney, Agent, or Firm*—Oliff & Berridge, PLC

(57) ABSTRACT

The present invention relates to a medicament delivery device such as an injector for self-administration of a medicament. Those using such devices are often infirm or have impaired vision. There is accordingly a dead for a medicament delivery device in which an amount of a dosage of medicament to be delivered can be selected relatively quickly by the firm and infirm alike and in which the amount of the dosage may readily be controlled and determined. Also there is a need to display the amount of the dialed dosage of medicament on the rotatable knob in figures sufficiently large and clear to be legible by those having a degree of impaired vision. There is disclosed a dose dial mechanism for a medicament delivery device having a housing, the dose dial mechanism comprising a dose dial element having a first thread for engagement with the housing and a dial sleeve member having a second thread for engagement with the housing; in which the dial sleeve member is coupled to the dose dial element so as to allow relative axial movement and inhibit relative rotational movement therebetween, and in which the pitch of the second thread is different from the pitch of the first thread so as to cause a different axial displacement of the dial sleeve member during axial displacement of the dose dial element.

4 Claims, 2 Drawing Sheets

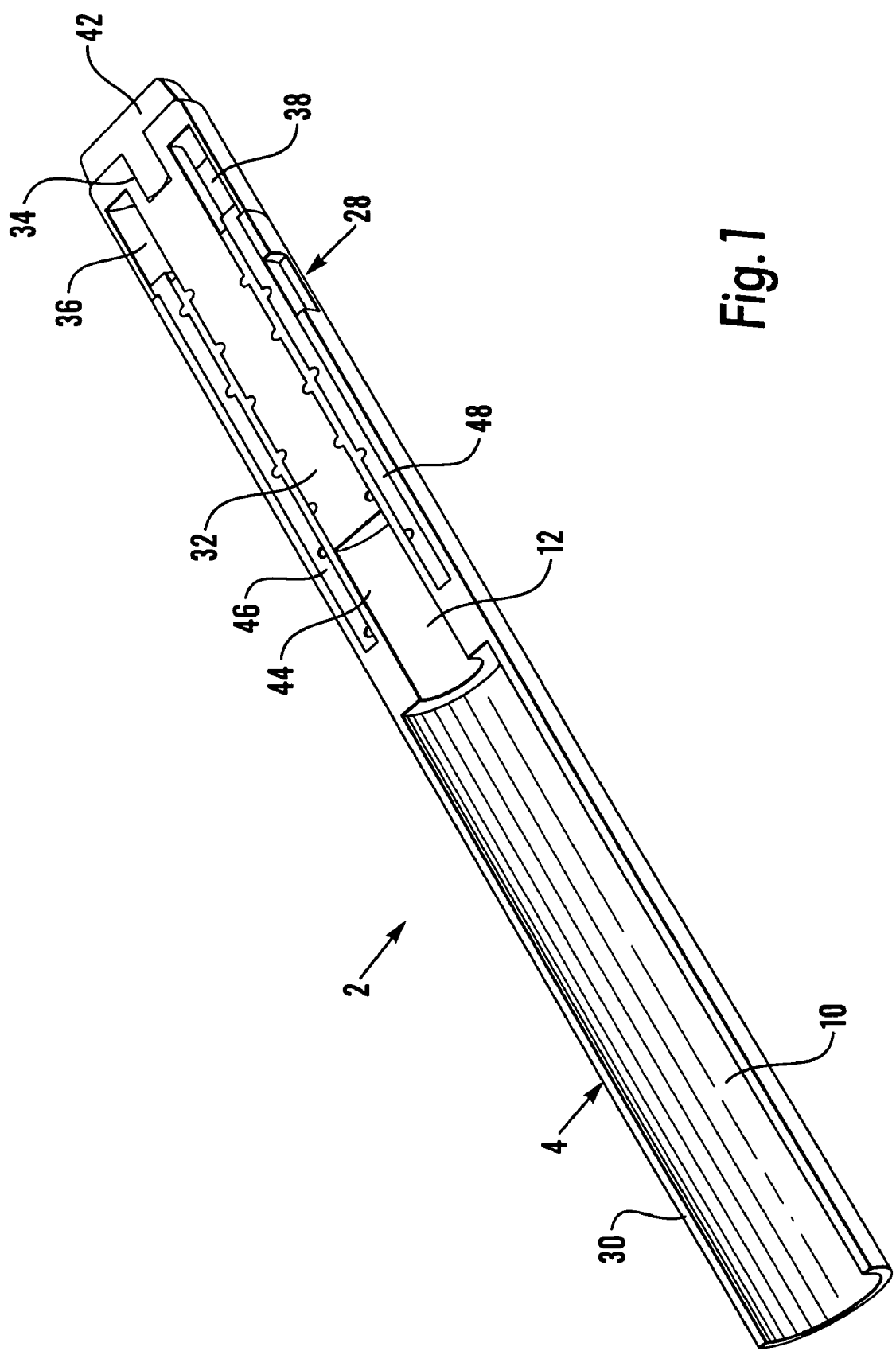

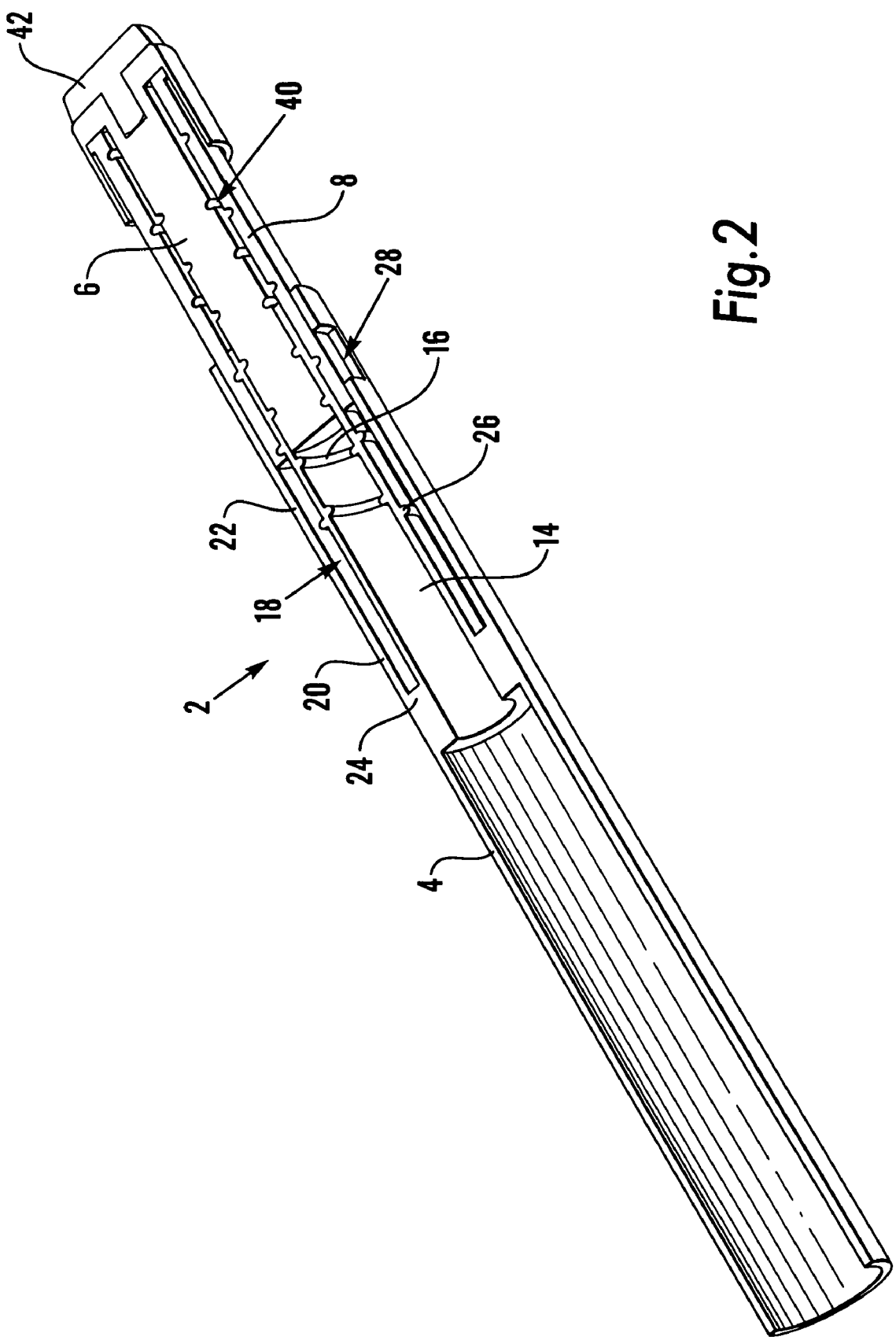

MEDICAMENT DELIVERY DEVICE

FIELD OF THE INVENTION

The present invention relates to a medicament delivery device, and in particular, but not exclusively, to a medicament delivery device such as an injector for self-administration of a medicament. Such injectors include those known as pen-type injectors.

BACKGROUND TO THE INVENTION

In the past, it was known for those requiring regular injections of a medicament, such as those having diabetes requiring injections of insulin, to use a syringe to remove a required amount of medicament from a phial, and then use the syringe to inject the required amount of medicament There are a number of drawbacks with this method. These include the fact that the loading of the syringe in this way is a delicate and somewhat skilled task, while those with, for example diabetes, are often infirm or have impaired vision, each of which increases the risk of inadvertent pricking upon the syringe. In addition, the use of syringes in public places has increasingly become socially unacceptable. To overcome these difficulties pen-type injectors have been developed.

Such injectors include within a main housing a medicament cartridge. The medicament cartridge is supplied loaded with a medicament. A user then selects a dosage and uses the pen-type injector to deliver the selected amount of medicament. The pen-type injectors are, as the name suggests, typically in the shape of a pen, though sometimes other forms are adopted. In each case, however, the appearance is non-descript so as not to draw attention to the device.

Often, the medicament Midge is replaceable to facilitate of the injector As noted above, those using such devices are often infirm or have impaired vision. There is accordingly a demand for a medicament delivery device in which an amount of a dosage of medicament to be delivered can be selected relatively quickly by the firm and infirm alike and in which the amount of the dosage may readily be controlled and determined.

It is known to provide a pen-type injector with a dose dial mechanism comprising a rotatable knob disposed at one end of the injector. The rotatable knob is connected either directly or indirectly with a drive means. The drive means acts upon a medicament cartridge located within the injector to cause medicament to be expelled from the injector. The rotatable knob conveniently comprises a helical dial. However, it is a problem with known devices of this type to display the amount of the dialed dosage of medicament on the rotatable knob in figures sufficiently large and clear to be legible by those users having a degree of impaired vision.

BRIEF DESCRIPTION OF THE INVENTION

According to a &at aspect of the invention, there is provided a dose dial mechanism for a medicament delivery device having a housing, the dose dial mechanism comprising:
   a dose dial element having a first tread for engagement with the housing;
   and a dial sleeve member having a second thread for engagement with the housing;
   wherein the dial sleeve member is coupled to the dose dial element so as to allow relative axial movement and inhibit relative rotational movement therebetween;
   and wherein the pitch of the second thread is different from the pitch of the first thread so as to cause a different axial displacement of the dial sleeve member during axial displacement of the dose dial element.

Preferably, the pitch of the second thread is greater than the pitch of the first thread. More preferably, the pitch of the second thread is one and one half times greater than the pitch of the first thread.

Advantageously, the dose dial element comprises a central shaft element having a first end and a second end, and including a radially outwardly directed flange at the first end of the shaft element, and a skirt depending from an end of the radially outwardly directed flange remote from s shaft element, such that the skirt, the radially outwardly directed flange and the first end of the shaft element define a groove at the first end of the shaft member and a first helical groove at the second end of the shaft element.

According to a second aspect of the invention a medicament delivery device comprises a dose dial mechanism according to the first aspect of the invention.

BRIEF DESCRIPTION OF THE DRAWINGS

The invention will now be described, by way of example only, with reference to the accompanying drawings, in which:

FIG. 1 shows a section tough a medicament delivery device in accordance with the present invention with the dose dial element and the dial sleeve member in a first position; and FIG. 2 shows a section similar to FIG. 1 with the dose dial element and the dial sleeve member in a second position.

DETAILED DESCRIPTION OF THE INVENTION

Referring to the Figures, here may be seen a section through a medicament delivery device 2 comprising a dose dial mechanism in accordance with the present invention. The medicament delivery device 2 comprises a generally elongate housing 4 of generally cylindrical configuration. At a first end of the housing 4 there is located the dose dial mechanism including a dose dial element 6 and a dial sleeve member 8.

Within the second end of the housing there is provided a cavity 10 with which a medicament cartridge (not shown) may be retained. It will be understood by those skilled in the art that the medicament delivery device will comprise further elements not shown in the drawings including but not limited to a needle unit and a cap for cover the needle unit when the medicament delivery device is not in use to prevent inadvertent pricking upon the needle unit.

The housing is provided at the first end with a bore 12 having a fixed diameter. Preferably, this diameter is less than that of the cavity 10. More preferably, this diameter is less than the diameter of an inner diameter of a medicament cartridge (not shown) housed within the second end of the housing 4. An inner surface 14 of the bore 12 is provided with a first screw thread 16 having a first fixed pitch.

Concentric with the bore 12 in the first end of the housing 4 there is provided an axially disposed groove 18. The axially disposed groove 18 comprises an inner surface 20, an outer surface 22 and a base surface 24 connecting the inner surface 20 and the outer surface 22. The inner surface 20 of the axially disposed groove 18 is provided with a second screw thread 26 having a second fixed pitch An opening 28 is provided through the outer surface 22 of the axially disposed groove 18 through to an outer surface 30 of the housing 4.

The dose dial element 6 and the dial sleeve member 8 are adapted to work within the first end of the housing 4. The dose dial element 6 and the dial sleeve member 8 are connected together in such a way as to inhibit or substantially prevent relative rotation therebetween such that rotation of the dose dial element 6 relative to the housing 4, for example by a user, causes a corresponding rotation of the dial sleeve member 8 relative to the housing 4. This may preferably be achieved by way of a spline arrangement (not shown) though any other suitable arrangement may be adopted.

In the illustrated embodiment, the dose dial element 6 may be seen to comprise a central shaft element 32 having a first end and a second end. The first end of the shaft element 32 is provided with a radially outwardly directed flange 34. A skirt 36 depends from an end of the radially outwardly directed flange 34 remote from the shaft element 32. The skirt 36, the radially outwardly directed flange 34 and the first end of the shaft element 32 in this way define an axially extending groove 38 at the first end of the shaft element 32. A first helical groove 40 is provided at the second end of the shaft element 32. The pitch of the first helical groove 40 is the same as that of the first screw thread 16. In use, the first screw thread 16 runs within the first helical groove 40.

In use, the second end of the shaft element 32 is adapted to drive a piston (not shown) located within a retained medicament cartridge (not shown) to expel a medicament from within the medicament cartridge.

In the illustrated embodiment a button 42, generally T-shaped in section, is provided in engagement with a suitably shaped recess in the first end of the dose dial element 6 such that the button 42 is able to freely rotate relative to the dose dial element 6. The button 42 may be of a softer material than the rest of the medicament delivery device to provide a more pleasing tactile experience for a user when operating the medicament delivery device 2.

The dial sleeve member 8 comprises a generally cylindrical member having an inner wall 44 and an outer wall 46. The inner wall 44 is provided with a second helical groove 48. The pitch of the second helical groove 48 is the same as that of the second screw thread 26. In use, the second screw thread 26 runs with the second helical groove 48. The dial sleeve member 8 is provided with a plurality of numbers (not shown) upon the outer wall 46 corresponding to a desired dosage to be dialed. The numbers are arranged in a generally helical pattern around the dial sleeve member 8, corresponding substantially to the second screw thread, such that each number becomes visible in turn Hugh the opening 28 in the housing 4 as the dose dial element 6 is rotated by a user, as described below.

In use, the dose dial mechanism is adapted to be moved between two extreme positions. In the first extreme position shown in FIG. 1, no dosage of medicament has been dialed and the skirt 36 of the dose dial element 6 is disposed adjacent, or substantially in abutment with, the it end of the housing 4. The dial sleeve member 8 is retained substantially within the axially disposed groove 18 of the housing 4, and extends only a small amount within the axially extending groove 38 of the dose dial element 6.

To dial a dosage of medicament to be delivered, the user twists or rotates the dose dial element 6 relative to the housing 4. The rotation of the dose dial element 6 relative to the housing 4 causes an axial movement of the dose dial element 6 relative to the housing 4 by virtue of the first screw tread 16. Thus, as the dose dial element 6 is rotated, it extends from the housing towards the second extreme position.

Furthermore, owing to the connection between the dose dial element 6 and the dial sleeve member 8 described above, the rotation of the dose dial element 6 causes a corresponding rotation of the dial sleeve member 8 relative to the housing 4. The rotation of the dial sleeve member 8 relative to the housing 4 also causes an axial movement of the dial sleeve member 8 relative to the housing 4 by virtue of the second screw thread. Thus, as the dial sleeve member 8 is rotated (through rotation of the dose dial element 6 by the user) it also extends from the housing 4 towards the second extreme position.

In the second extreme position shown in FIG. 2, a maximum dosage of medicament has been dialed. The skirt of the dose dial element 6 is disposed a distance from the first end of the housing 4 while the dial sleeve member 8 extends from within the axially disposed groove 18 of the housing 4. In this position, the dial sleeve member 8 substantially fills the axially disposed groove 18 of the housing 4.

It will be appreciated tat, owing to the difference in pitch between the first and second screw threads, the axial movement of the dose dial element 6 relative to the housing 4 will be rent from that of the dial sleeve member 8. In a preferred embodiment the pitch of the second screw thread 26 is 1.5 times greater than the pitch of the first screw tread 16. Thus, when the dose dial element 6 is rotated by the user, the dial sleeve member 8 moves 1.5 times greater along its axis than the dose dial element 6.

Since the dial sleeve member a moves a greater distance than the dose dial element 6, each of the dosage numbers may be spaced further apart from one another or made larger than if the dosage numbers were to be located directly upon a drive member or upon the dose dial element itself.

To deliver the dosage of medicament, the user presses tie button 42 to exert an axial force on the dose dial element 6 thereby to cause the dose dial mechanism to move axially towards the first extreme position. As the dose dial mechanism moves towards the first extreme position, the dose dial element 6 engages with the piston located within the retained medicament cartridge thereby to expel the medicament from the cartridge.

In addition, as the dose dial mechanism moves towards the first extreme position, the first thread 16 causes the dose dial element 6 to rotate relative to the housing 4 while the second thread and the non-rotatable connection between the dose dial element 6 and the dial sleeve member 8 cause the dial sleeve member to rotate relative to the housing 4.

The rotatable engagement of the button 42 with the dose dial element 6 allows the former to remain rotationally fixed relative to the user as the latter rotates thereby to permit easier movement of the dose dial mechanism.

Once again, the increased pitch of the second screw thread compared with the first screw tread causes the dial sleeve member 8 to move further axially than the dose dial element 6, thereby to return the dose dial mechanism to the first extreme position as shown in FIG. 1.

The invention claimed is:

1. A medicament delivery device comprising:
    a housing; and
    a dose dial mechanism, the dose dial mechanism comprising:
        a dose dial element having a first thread that engages the housing; and a dial sleeve member having a second thread that engages the housing;

wherein the dial sleeve member is coupled to the dose dial element so as to allow relative axial movement and inhibit relative rotational movement therebetween;

and wherein the pitch of the second thread is different from the pitch of the first thread so as to cause a different axial displacement of the dial sleeve member during axial displacement of the dose dial element.

2. The device according to claim 1, in which the pitch of the second thread is greater than the pitch of the first thread.

3. The device according to claim 2, in which the pitch of the second thread is one and one half times greater than the pitch of the first thread.

4. The device according to claim 1, in which the dose dial element comprises a central shaft element having a first end and a second end, and including a radially outwardly directed flange at the first end of the shaft element, and a skirt depending from an end of the radially outwardly directed flange remote from the shaft element, such that the skirt, the radially outwardly directed flange and the first end of the shaft element define a groove at the first end of the shaft member and a first helical groove at the second end of the shaft element.

* * * * *